(12) United States Patent
Tagade et al.

(10) Patent No.: US 11,721,413 B2
(45) Date of Patent: Aug. 8, 2023

(54) METHOD AND SYSTEM FOR PERFORMING MOLECULAR DESIGN USING MACHINE LEARNING ALGORITHMS

(71) Applicant: SAMSUNG ELECTRONICS CO., LTD., Suwon-si (KR)

(72) Inventors: Piyush Tagade, Bangalore (IN); Shanthi Pandian, Bangalore (IN); S Krishnan Hariharan, Bangalore (IN); Parampalli Shashishekara Adiga, Bangalore (IN)

(73) Assignee: SAMSUNG ELECTRONICS CO., LTD., Gyeonggi-do (KR)

( * ) Notice: Subject to any disclaimer, the term of this patent is extended or adjusted under 35 U.S.C. 154(b) by 1160 days.

(21) Appl. No.: 16/376,132

(22) Filed: Apr. 5, 2019

(65) Prior Publication Data

US 2019/0325983 A1 Oct. 24, 2019

(30) Foreign Application Priority Data

Apr. 24, 2018 (IN) .......................... IN201841015526
Oct. 2, 2018 (KR) .......................... 10-2018-0117878

(51) Int. Cl.
| | | |
|---|---|---|
| *G16C 20/50* | (2019.01) | |
| *G16C 20/70* | (2019.01) | |
| *G06N 20/20* | (2019.01) | |
| *G06N 7/08* | (2006.01) | |
| *G06N 7/01* | (2023.01) | |
| *G06N 5/04* | (2023.01) | |
| *G06N 3/047* | (2023.01) | |
| *G06N 3/045* | (2023.01) | |

(52) U.S. Cl.
CPC ............. *G16C 20/50* (2019.02); *G06N 3/045* (2023.01); *G06N 3/047* (2023.01); *G06N 5/04* (2013.01); *G06N 7/01* (2023.01); *G06N 7/08* (2013.01); *G06N 20/20* (2019.01); *G16C 20/70* (2019.02)

(58) Field of Classification Search
CPC .......... G16C 20/50; G16C 20/70; G06N 5/04; G06N 7/005; G06N 7/08; G06N 20/20; G06N 3/0454; G06N 3/0472; G06N 3/08
See application file for complete search history.

(56) References Cited

U.S. PATENT DOCUMENTS

| | | | |
|---|---|---|---|
| 7,702,467 B2 | 4/2010 | Duffy | |
| 7,856,321 B2 | 12/2010 | Lanza et al. | |
| 2016/0196412 A1 | 7/2016 | Hopkins et al. | |
| 2019/0018933 A1* | 1/2019 | Oono ....................... | G06N 7/08 |

OTHER PUBLICATIONS

Blaschke, T., Olivecrona, M., Engkvist, O., Bajorath, J. and Chen, H. Application of generative autoencoder in de novo molecular design. Molecular informatics, 37(1-2), p. 1700123. (Year: 2018).*
Jain, A., Hautier, G., Moore, C.J., Ong, S.P., Fischer, C.C., Mueller, T., Persson, K.A. and Ceder, G. A high-throughput infrastructure for density functional theory calculations. Computational Materials Science, 50(8), pp. 2295-2310. (Year: 2011).*
Arun Mannodi-Kanakkithodi et al., Machine Learning Strategy for Accelerated Design of Polymer Dielectrics, Scientific Reports, 2016, pp. 1-10.
David Weininger, Smiles, a chemical language and information system, 1988, 28: 31-36, J Chem Inf Comput Sci.
Hae Sung Lee, [Science] Computer design?. . . Molecular design technology led by new drug development, News, Article, retreived on Jun. 7, 2019, 7pages, http://news.hankyung.com/article/2010120908911.
Kyunghyun Cho et al., Gaussian-Bernoulli Deep Boltzmann Machine, 2013, 7 pages, Neural Networks (IJCNN).
Min Sik Park et al., A search map for organic additives and solvents applicable in high-voltage rechargeable batteries, PAPER, 2016, 18, pp. 26807-26815, PCCP, Royal Society of Chemistry.
Rafael Gomez-Bombarelli et al., Automatic Chemical Design Using a Data-Driven Continuous Representation of Molecules, Research Article, 2018, 4, pp. 268-276, ACS central science.
Ruslan Salakhutdinov et al., Deep Boltzmann Machines, 2009, pp. 448-455, Artificial Intelligence and Statistics.

* cited by examiner

*Primary Examiner* — Lori A. Clow
*Assistant Examiner* — Janna Nicole Schultzhaus
(74) *Attorney, Agent, or Firm* — Cantor Colburn LLP

(57) ABSTRACT

The embodiments herein disclose a method and system for designing molecules by using a machine learning algorithm. The method includes representing molecular structures included in a dataset by using a Simplified Molecular Input Line Entry System (SMILES), where the SMILES uses a series of characters, converting a SMILES representation of the molecular structures into a binary representation, pre-training a stack of Restricted Boltzmann Machines (RBMs) by using the binary representation of the molecular structures, constructing a Deep Boltzmann Machine (DBM) by using the stack of the RBMs, determining limited molecular property data for a subset of the molecule structures in the dataset, training the DBM with the limited molecular property data, combining the pre-trained stack of the RBMs and the trained DBM in a Bayesian inference framework, and generating a sample of molecules with target properties by using the Bayesian inference framework.

12 Claims, 8 Drawing Sheets

METHOD AND SYSTEM FOR PERFORMING MOLECULAR DESIGN USING MACHINE LEARNING ALGORITHMS

CROSS-REFERENCE TO RELATED APPLICATIONS

This application claims priority to Indian Patent Application No. 201841015526, filed on Apr. 24, 2018, in the Indian Patent Office and Korean Patent Application No. 10-2018-0117878, filed on Oct. 2, 2018, in the Korean Intellectual Property Office, and all the benefits accruing therefrom under 35 U.S.C. § 119, the content of which in their entirety are herein incorporated by reference.

BACKGROUND

1. Field

The disclosure relates to a method and system for performing molecular design using machine learning algorithms. More particularly, the disclosure relates to a molecular design field, specifically, attribute driven inverse molecular design using a deep learning Bayesian framework.

2. Description of the Related Art

Existing mechanisms use evolutionary optimization methods for molecular design, which are acquired from expert information to obtain structure-property correlation and use molecular fingerprints designed by experts. Further, the mechanisms use a supervised shallow machine learning approach to obtain structure-property correlation. However, the mechanisms require a large dataset for acceptable accuracy. Also, the mechanisms may suggest infeasible molecules.

In another existing mechanism, a machine learning method is used to obtain a structure-property correlation, which solves only a forward property prediction problem. The method also uses molecular fingerprints designed by experts and the supervised shallow machine learning approach.

In another existing mechanism, a ranking based method is used for the creation of an optimal training set for the machine learning technique.

SUMMARY

Provided are a method and system for designing molecules by using a machine learning algorithm.

Additional aspects will be set forth in part in the description which follows and, in part, will be apparent from the description, or may be learned by practice of the presented embodiments.

According to an embodiment, a method for designing molecules using a machine learning algorithm includes representing, by a Simplified Molecular Input Line Entry System ("SMILES") representation unit, molecular structures in a dataset including the molecular structures using a SMILES, where the SMILES uses a set of characters, converting, by a binary representation unit, a SMILES representation of the molecular structures into a binary representation, pre-training, by a molecular structure generating unit, a stack of Restricted Boltzmann Machines ("RBMs") using the binary representation of the molecular structures, constructing, by the molecular structure generating unit, a Deep Boltzmann Machine ("DBM") using the stack of the RBMs, determining, by the molecular structure generating unit, limited molecular property data by running a Density Functional Theory ("DFT") on a subset of the molecule structures in the dataset, training, by the molecular structure generating unit, the DBM with the limited molecular property data, combining, by the molecular structure generating unit, the pre-trained stack of RBMs with the trained DBM in a Bayesian inference framework, and generating, by the molecular structure generating unit, a sample of molecules with target properties using the Bayesian inference framework.

According to another embodiment, a system for designing molecules using a machine learning algorithm includes a SMILES representation unit which represents molecular structures in a dataset including the molecular structures using a Simplified Molecular Input Line Entry System (SMILES), where the SMILES uses a set of characters, a binary representation unit which converts a SMILES representation of the molecular structures into a binary representation, a molecular structure generating unit which pre-trains a stack of Restricted Boltzmann Machines (RBMs) using the binary representation of the molecular structures, constructs a Deep Boltzmann Machine (DBM) using the stack of the RBMs, determines limited molecular property data by running a Density Functional Theory (DFT) on a subset of the molecule structures in the dataset, trains the DBM with the limited molecular property data, combines the pre-trained stack of RBMs with the trained DBM in a Bayesian inference framework, and generates a sample of molecules with target properties using the Bayesian inference framework.

BRIEF DESCRIPTION OF THE DRAWINGS

These and/or other features will become apparent and more readily appreciated from the following description of the embodiments, taken in conjunction with the accompanying drawings in which.

DETAILED DESCRIPTION

Figure 1:
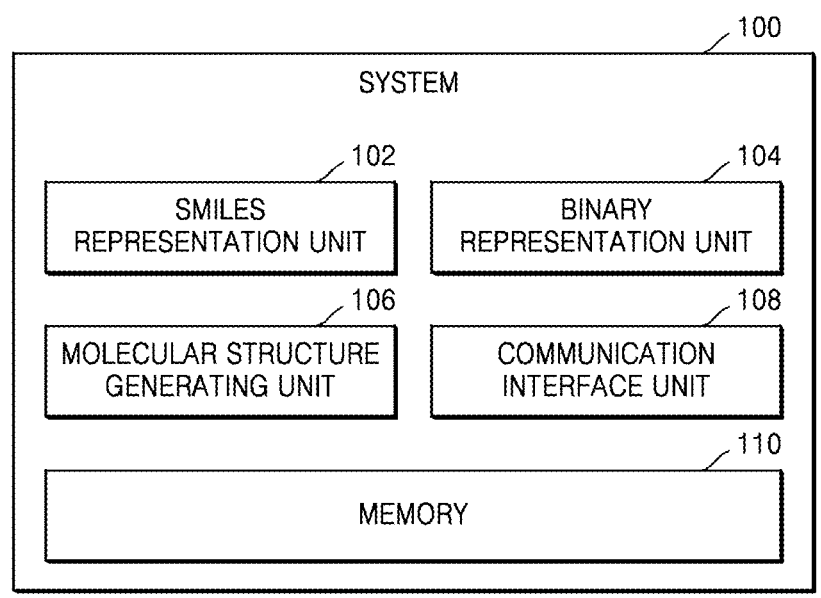
FIG. 1 is a block diagram illustrating a system including various units, according to an embodiment.

Although general terms being widely used in the related art were selected as the terminology used in the present embodiments while considering the functions of the present embodiments, they may vary according to intentions of one of ordinary skill in the art, judicial precedents, the advent of new technologies, and the like. Terms arbitrarily selected by the applicant of the present disclosure may also be used in a specific case. In this case, their meanings will be described in the detailed description of the corresponding embodiment. Hence, the terms used in the present embodiments must be defined based on the meanings of the terms and the contents of the entire specification, not by simply stating the terms themselves.

In this specification, it will be understood that the case in which a certain part is "connected" to another part includes the case in which the part is "electrically connected" to the other part with an intervening component, as well as the case in which the part is "directly connected" to the other part. Also, it will be understood that when a certain part "includes" a certain component, the part does not exclude another component but can further include another component, unless the context clearly dictates otherwise. As used herein, the term "portion", "module", or "unit" refers to a unit that can perform at least one function or operation, and may be implemented as hardware or software or as a combination of hardware and software.

Also, the term "configured" or "include" as used in the current embodiments should not be interpreted as a meaning necessarily including all of components or operations in this specification. That is, some of the components or some of the operations may be omitted, or additional components or operations may be further included.

The terminology used herein is for the purpose of describing particular embodiments only and is not intended to be limiting. As used herein, the singular forms "a," "an," and "the" are intended to include the plural forms, including "at least one," unless the content clearly indicates otherwise. "At least one" is not to be construed as limiting "a" or "an." "Or" means "and/or." As used herein, the term "and/or" includes any and all combinations of one or more of the associated listed items.

The following description about the embodiments should not be interpreted as limiting the scope of a right, and techniques that can be easily inferred by one of ordinary skill in the art should be interpreted as belonging to the scope of a right of the embodiments. Hereinafter, the exemplary embodiments will be described in detail with reference to the accompanying drawings.

The embodiments disclose a method and system for designing molecules using a machine learning algorithm.

An embodiment may include an operation of representing every molecule of a large dataset of molecular structures using a Simplified Molecular Input Line Entry System ("SMILES"). Here, the SMILES may use a set of characters to represent every molecule of the large dataset of molecular structures.

Also, an embodiment may include an operation of converting the SMILES representation of every molecule of the large dataset of molecular structures into a binary representation.

Also, an embodiment may include an operation of pre-training a stack of Restricted Boltzmann Machines ("RBMs") using the binary representation of the large dataset of molecular structures to construct a Deep Boltzmann Machine ("DBM").

Also, an embodiment may include an operation of determining limited molecular property data for a subset of molecule structures in the large dataset of molecular structures and an operation of training the DBM with the limited molecular property data. Here, the limited molecular property data may be obtained by running Density Functional Theory ("DFT") on the subset of molecule structures. DFT is a computational quantum mechanical modelling method used in physics, chemistry and materials science to investigate the electronic structure of many-body systems, in particular atoms, molecules, and the condensed phases.

Also, an embodiment may include an operation of combining the pre-trained stack of RBMs and the trained DBM with the limited molecular property data in a Bayesian inference framework to generate a sample of molecules with target properties.

FIG. 1 is a block diagram illustrating a system including various units, according to an embodiment.

A system 100 may be at least one of, but not restricted to, a mobile phone, a smartphone, a tablet, a phablet, a personal digital assistant ("PDA"), a laptop, a computer, a wearable computing device, an Internet of Things ("IoT") device, a computing device, and so on.

An embodiment may provide the system 100 for designing molecules.

The system 100 may include a SMILES representation unit 102, a binary representation unit 104, a molecular structure generating unit 106, a communication interface unit 108 and a memory 110.

The communication interface unit 108 may be configured to establish communication between the system 100 and an external molecular structure database. Here, the external molecular database may include a large dataset of molecular structures, and experimental properties and calculated properties of the subset (i.e., small data subset) of molecule structures of the large dataset of molecular structures.

The SMILES representation unit 102 may be configured to represent every molecule of a large dataset of molecular structures using the SMILES. Here, the SMILES may use a set of characters to represent every molecule of the large dataset of molecular structures. For example, using the SMILES, a Benzene ring is represented as C1=CC=CC=C1.

The binary representation unit 104 may be configured to convert a SMILES representation of every molecule of the large dataset of molecular structures into a binary representation. Further, the binary representation unit 104 may be configured to convert each character of the SMILES representation to its equivalent ASCII representation, which is subsequently converted to a binary number.

The molecular structure generating unit 106 may be configured to pre-train a stack of RBMs using the binary representation of the large dataset of molecular structures to construct a DBM. Further, the molecular structure generating unit 106 may be configured to determine limited molecular property data for a subset of molecule structures in the large dataset of molecular structures and train the DBM with the limited molecular property data. Here, the limited molecular property data may be obtained by running the DFT on the subset of molecule structures.

Further, the molecular structure generating unit 106 may be configured to combine the pre-trained stack of RBMs and the trained DBM with the limited molecular property data in a Bayesian inference framework to generate a sample of molecules with target properties.

An embodiment may further include an operation of determining a sample of molecules with target properties and substructures using Markov Chain Monte Carlo ("MCMC") sampling.

An embodiment may further include an operation of storing parameters of the pre-trained RBMs to design advanced materials for any new application.

An embodiment may further include an operation of predicting properties for a given molecule using the trained DBM.

An embodiment may further include an operation of guiding the user to perform calculations/experiments for new molecules.

Also, an embodiment may further include an operation of constructing a valid molecular structure using the pre-trained RBM.

Designing molecules with target properties may play a critical role in improving the performance and safety of engineering systems. For example, a performance and safety of lithium-ion batteries may be significantly improved by designing electrolytes with target redox stability and conductivity. The embodiments herein may disclose a method and system for generating molecular structures having targeted physical, chemical, optoelectronic, functional, and/or bioactive properties.

An initial population of molecules may be provided in terms of a representation of a number of member molecules, and provided to acquire and analyze one or more physical, chemical, functional and/or bioactive properties of these molecules to synthesize structure-property relationships.

The structural information may be digitally synthesized using SMILES based graph-theoretic representations, and the structure-property relationships may be processed using the DBM. Then, an inverse molecular design approach may be used to generate a set of molecules with one or more physical, chemical, optoelectronic, functional and/or bioactive properties in a desired/specified range.

In an embodiment herein, an attribute-driven molecular/chemical structure design may be based on the Bayesian Inference approach.

Further, in an embodiment, the accuracy of these inverse predictions may be improved by using automated, targeted validation through theoretical calculations.

The method and system 100 disclosed in the embodiments may use a fully-automated artificial intelligence ("AI") based approach with no human intervention required.

Further, the method and system 100 disclosed in the embodiments may use a semi-supervised deep learning approach with minimal property data.

The method and system 100 disclosed in the embodiments may be used for attribute-driven molecule design for a variety of applications. Further, the conditional MCMC sampling may correct the backbone for molecule design.

The memory 110 may be configured to store the SMILES representation of the large dataset of molecular structures. Further, the memory 110 may be configured to store the binary representation of the molecular structures. Further, the memory 110 may be configured to store the sample of molecules with target properties.

The memory 110 may include one or more computer-readable storage media. The memory 110 may include non-volatile storage elements. Examples of such non-volatile storage elements may include magnetic hard discs, optical discs, floppy discs, flash memories, or forms of electrically programmable memories ("EPROM") or electrically erasable and programmable ("EEPROM") memories.

In addition, the memory 110 may, in an embodiment, be considered as a non-transitory storage medium. The term "non-transitory" may indicate that the storage medium is not embodied in a carrier wave or a propagated signal. However, the term "non-transitory" should not be interpreted to mean that the memory 110 is non-movable. In an embodiment, a non-transitory storage medium may store data that can, over time, change (e.g., in Random Access Memory ("RAM") or cache).

FIG. 1 shows exemplary a system 100 including various units, but it is to be understood that other embodiments are not limited thereon. In other embodiments, the system 100 may include less or more number of units. Further, the labels or names of the units are used only for illustrative purpose and does not limit the scope of the embodiments herein. One or more units may be combined to perform the same or substantially similar function in the system 100.

Figure 2:
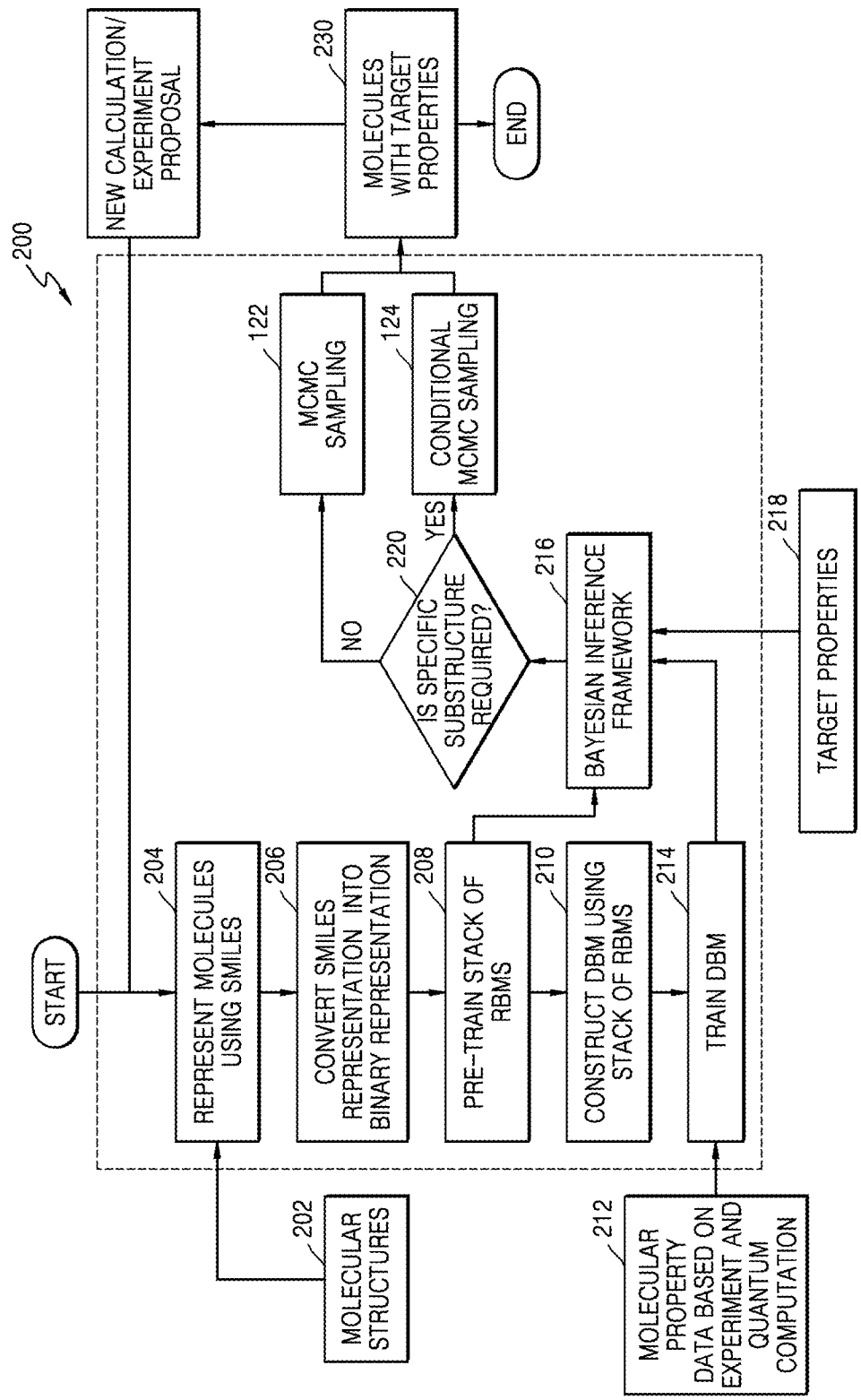
FIG. 2 is a flowchart illustrating a method of designing molecules, according to an embodiment.

FIG. 2 is a flowchart illustrating a method of designing molecules, according to an embodiment.

In operation 202, the method may include collecting/receiving one or more large datasets of molecular structures from the external molecular structure database, for example, a PubChem database. The method may allow the system 100 to collect the large datasets of molecular structures from the external molecular structure database.

In operation 204, the method may include representing every molecular structure using the SMILES. The operation may allow the SMILES representation unit 102 to represent every molecular structure using the SMILES. The SMILES may use a set of characters to represent a molecule structure. For example, a Benzene ring may be represented using the SMILES as C1=CC=CC=C1.

In operation 206, the method may include converting the SMILES representation of every molecule of the large dataset of molecular structures into a binary representation. The method may allow the binary representation unit 104 to convert the SMILES representation of every molecule of the large dataset of molecular structures into the binary representation. Each character of the SMILES representation may be converted to its equivalent ASCII representation, which is subsequently converted to the binary number.

In operation 208, the method may include pre-training a stack of RBMs using the binary representation of the large dataset of molecular structure. A contrastive divergence algorithm may be used for pre-training the stack of RBMs. According to an embodiment, the method may allow the molecular structure generating unit 106 to pre-train the stack of RBMs using the binary representation of the large dataset of molecular structures.

In operation 210, the method may include constructing a DBM by stacking the pre-trained RBMs together. According to an embodiment, the method may allow the molecular structure generating unit 106 to construct the DBM by stacking the pre-trained RBMs together.

In operation 212, the method may include determining limited molecular property data for a subset of molecule structures of the large dataset of molecular structures. According to an embodiment, the method may allow the molecular structure generating unit 106 to determine the limited molecular property data for the subset of molecule structures of the large dataset of molecular structures. The limited molecular property data may be determined based on quantum computation and experiment results acquired by running the DFT on the subset of molecule structures.

In operation 214, the method may include training the DBM with the limited molecular property data. The method may allow the molecular structure generating unit 106 to train the DBM with the limited molecular property data. This trained DBM may be used to predict properties of any molecule, given its molecular structure.

In operation 216, the method may include combining the pre-trained stack of RBMs and the trained DBM with the limited molecular property data in a Bayesian inference framework to generate a sample of molecules with target properties. According to an embodiment, the method may allow the molecular structure generating unit 106 to combine the pre-trained stack of RBMs and the trained DBM with the limited molecular property data in a Bayesian inference framework to generate a sample of molecules with target properties.

In operation 218, the method may include determining target properties specified by the user for a given application. According to an embodiment, the method may allow the molecular structure generating unit 106 to determine target properties specified by the user for a given application. The system 100 may be configured to receive the target properties as a user input. Further, based on the target properties, the molecular structure generating unit 106 may be configured to determine target properties specified by the user for a given application. For example, desired reduction and oxidation potential values as the target properties may be specified for designing stable electrolytes for Li-ion batteries.

In operation 220, the method may include determining whether a specific substructure is required. This substructure may be specified based on the user requirements.

In operation 220, in a case that the molecular structure generating unit 106 determines that no specific substructure is required, in operation 122, the molecular structure generating unit 106 may use the MCMC method to determine a set of molecules with target properties from a posterior distribution of the Bayesian inference.

In operation 220, in a case that the molecular structure generating unit 106 determines that a specific substructure is required, in operation 124, the molecular structure generating unit 106 may use the conditional MCMC sampling to obtain such molecules (e.g., molecules with the target properties and substructures). For example, if molecules with certain fixed attributes, like fixed ethylene oxide at the end of a chain of a polymer, are desired, the conditional MCMC sampling may be used to obtain such molecules.

In operation 230, the memory 110 may store the sample of molecules with target properties. In addition, a real sample of molecules with target properties may be generated by using various manufacturing methods.

The various actions, acts, operations, or the like in the flow diagram 200 may be performed in the order presented, in a different order or simultaneously.

Further, in some embodiments, some of the actions, acts, blocks, operations, or the like may be omitted, added, modified, skipped, or the like without departing from the scope of the invention.

Figure 3:
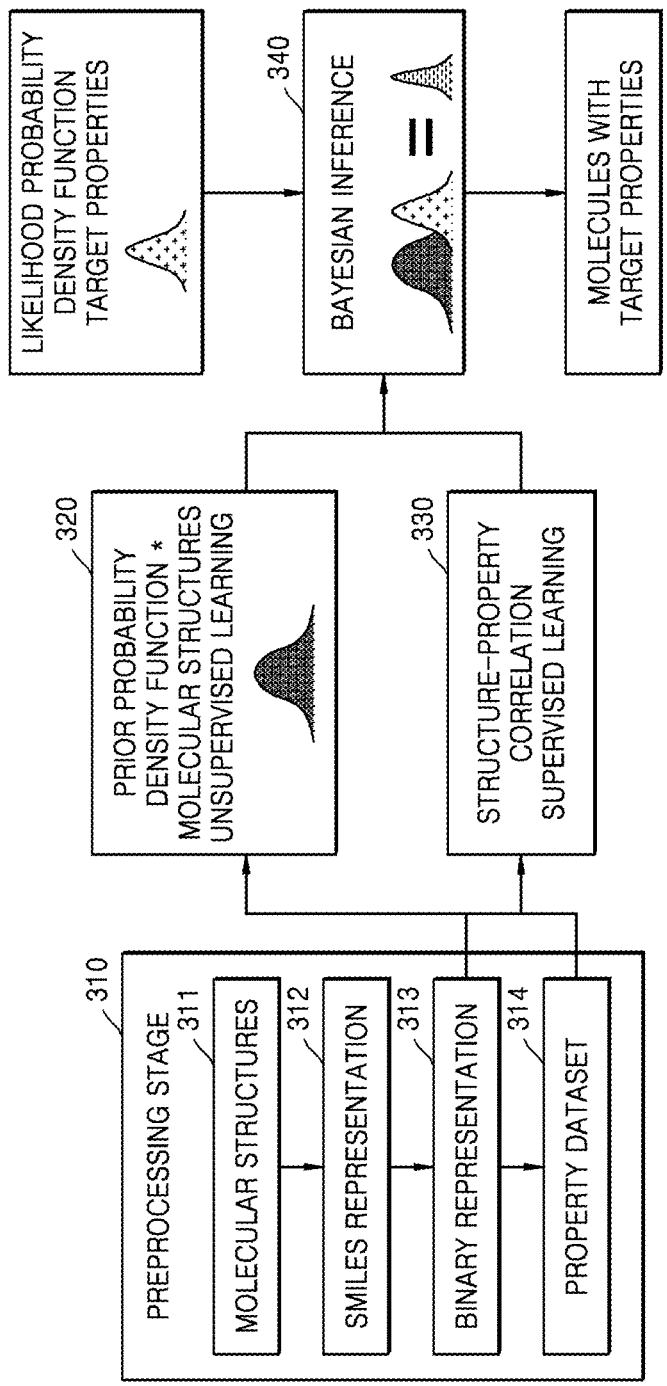
FIG. 3 is a flow diagram illustrating a deep learning Bayesian framework for designing molecules, according to an embodiment.

FIG. 3 is a flow diagram illustrating a deep learning Bayesian framework for designing molecules, according to an embodiment.

The deep learning Bayesian framework may include a preprocessing stage 310 including operations 311, 312, 313, and 314.

In operation 311, a large dataset of molecular structures may be collected from an external molecular structure database.

In operation 312, structures of molecules included in the large dataset may be represented using the SMILES. Here, the SMILES may use a set of characters to represent the molecule structures.

In operation 313, a SMILE representation of the molecules included in the large dataset may be converted into a binary representation. More specifically, each character of the SMILES representation may be converted to its equivalent ASCII representation, which is subsequently converted to an 8-bit binary number.

In operation 314, the system 100 may decide a property dataset from a small data subset including molecular structures.

In operation 320, an 8-bit binary number may be used to train a machine learning method known as RBM in an unsupervised learning manner. Also, as not shown in the flow diagram, another RBM may be trained in a supervised learning manner using the property dataset decided from the small data subset. The RBM is known as Gaussian-Bernoulli Restricted Boltzmann Machine ("GBRBM"), which is also a machine learning method.

Also, in operation 330, the system 100 may combine a stack of RBMs, which has trained using the binary representation of molecules with the GBRBM, which was trained using the property dataset to construct the DBM. Further, the system 100 may train the DBM with the combined RBM and GBRBM in the supervised learning manner. By training the DBM, information about the correlation between molecular structures and properties may be acquired, and therefore, properties of the given molecules may be predicted.

In operation 340, the molecular structure generating unit 106 of the system 100 may combine the pre-trained stack of RBMs and the trained DBM with the limited molecular property data in a Bayesian inference framework to generate a sample of molecules with target properties.

The Bayesian framework uses a principle, which states that posterior probability is directly proportional to likelihood probability multiplied by prior probability. The prior probability may indicate existing knowledge about given molecular structures. The prior probability may indicate whether the given molecular structures are valid molecular structures or not. The likelihood probability may indicate a probability distribution of target properties. The likelihood probability may be defined in terms of what all properties required for a new application. The likelihood probability may be determined by the DBM.

Figure 4:
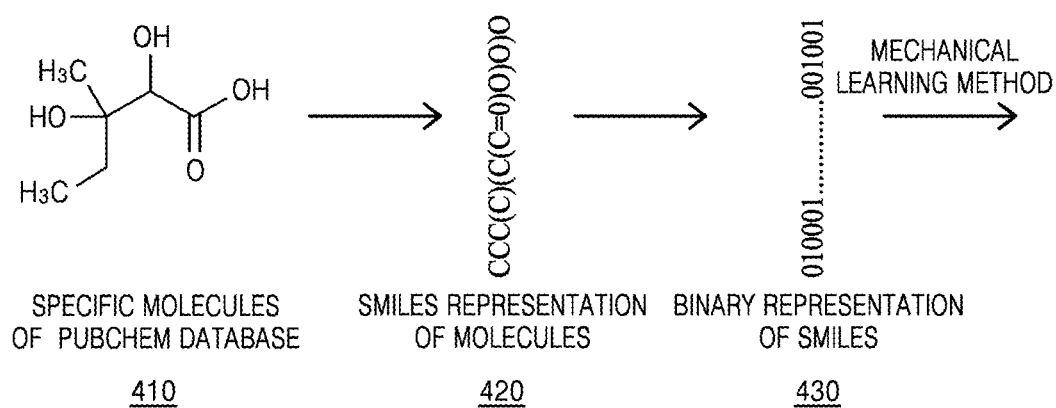
FIG. 4 illustrates a Simplified Molecular Input Line Entry System (SMILES) representation of molecules, according to an embodiment.

FIG. 4 illustrates a SMILES representation of molecules, according to an embodiment. The SMILES may be an input for designing molecules with target properties.

In operation 410, the molecules and the respective properties of the molecules may be obtained from different databases (for example, PubChem, KHAZANA or the like).

In operation 420, the molecules may be represented using the SMILES, and a SMILES representation of the molecules may allow identification of molecular structures.

In operation 430, each character in the SMILES representation may be converted to an 8-bit binary variable. More specifically, each character of the SMILES representation may be first converted to its corresponding ASCII representation. Subsequently, the ASCII representation may be converted to an equivalent 8-bit binary number. The 8-bit binary number may be used in a machine learning process.

Figure 5:
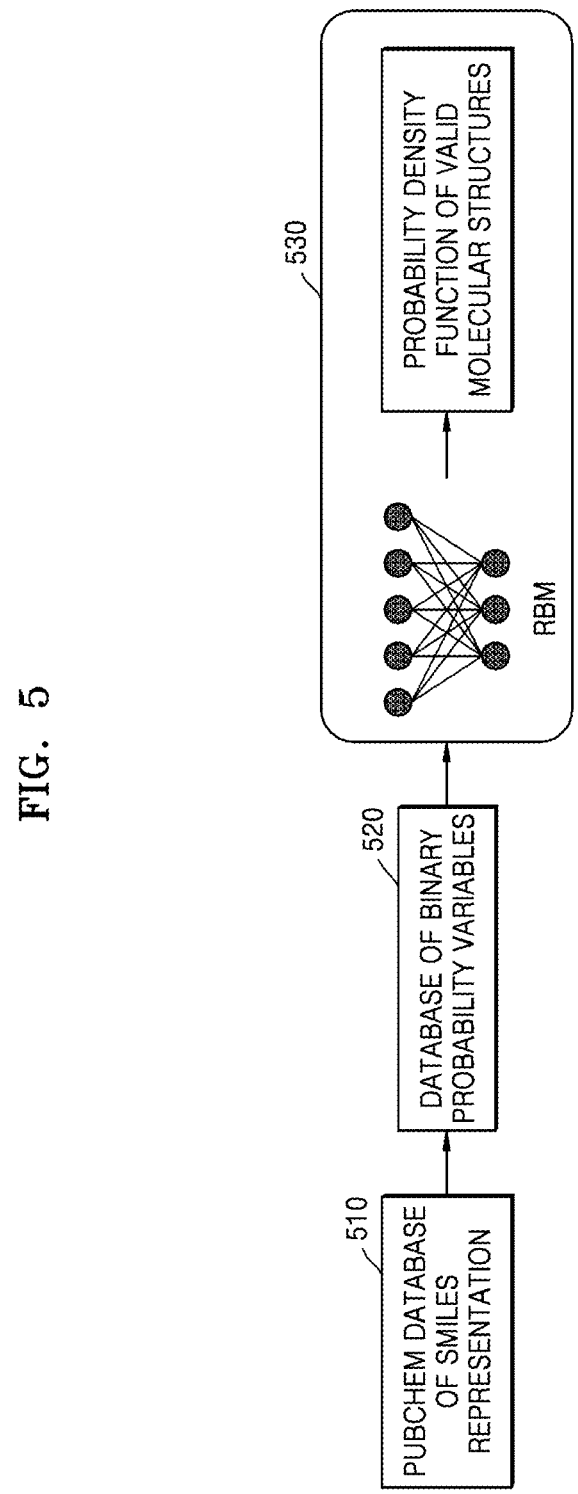
FIG. 5 is a flow diagram illustrating unsupervised learning of molecular structures using a Restricted Boltzmann Machine (RBM), according to an embodiment.

FIG. 5 is a flow diagram illustrating unsupervised learning of a molecular structure using an RBM, according to an embodiment.

An embodiment herein may include estimating probability at which a structure of a candidate molecule predicted to have target properties will be a valid molecular structure.

In operation 510, the system 100 may represent the molecular structure using the SMILES. Here, the SMILES may use a set of characters to represent every molecule of large data (for example, PubChem database).

In operation 520, the system 100 may convert the SMILES representation of the molecular structures into a binary representation (i.e., a database of binary random variables).

In operation 530, the system 100 may include training the RBM (i.e., through Deep Belief Network ("DBN")) using the binary representation of the molecular structures to determine a probability density function of the molecular structures so as to determine whether the molecular structures are valid molecular structures or not.

Figure 6:
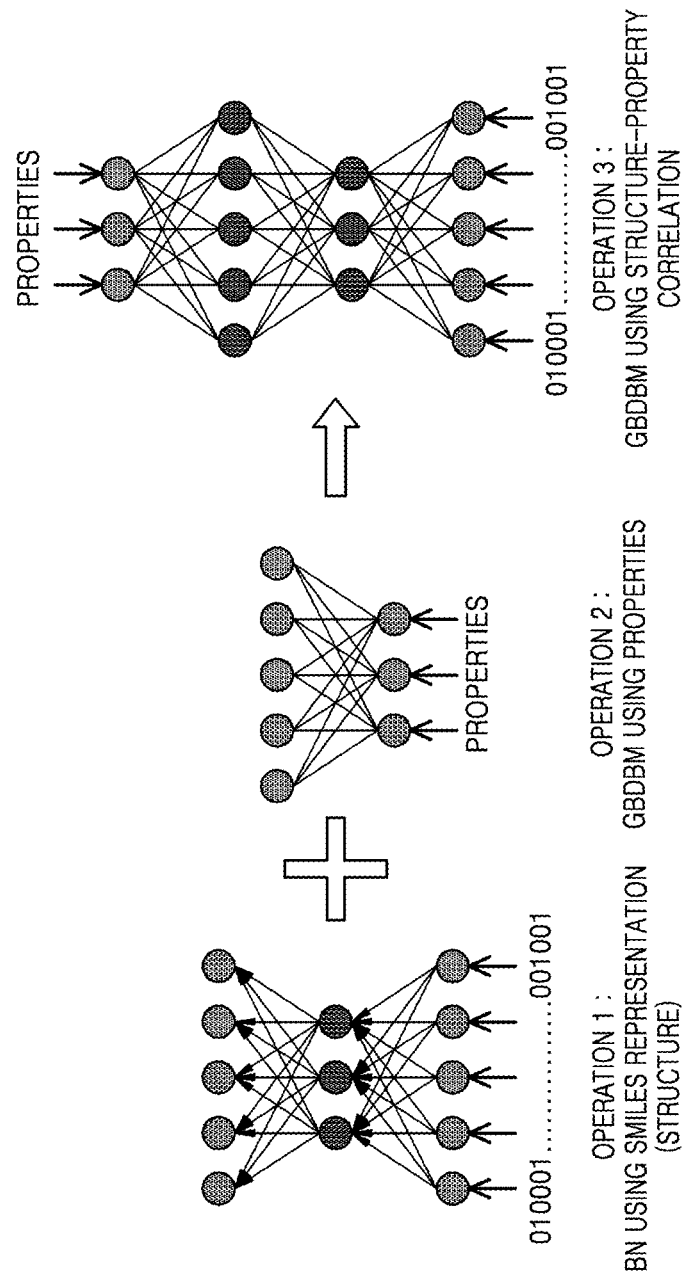
FIG. 6 is a schematic diagram illustrating a construction of a Deep Boltzmann machine (DBM) using a Restricted Boltzmann Machine (RBM) to predict properties for given molecules, according to an embodiment.

FIG. 6 is a schematic diagram illustrating a construction of a DBM using an RBM to predict properties for given molecules, according to an embodiment.

An embodiment may predict properties for a given molecule structure using the DBM. Operations involved in predicting the properties for the given molecule structure are as follows:

Operation 1: Multi-layer Deep Belief Network (DBN) may be used for training the molecular structure. An embodiment may represent a molecular structure using the SMILES. Here, the SMILES may use a set of characters to represent every molecule of a large dataset of molecular structures. Further, an embodiment may include converting the SMILES representation of molecular structures into a binary representation. Further, an embodiment may include training a stack of RBMs (i.e., DBN) using the binary representation of the molecular structures.

Operation 2: 2-layer RBM may be used for training properties (e.g., conductivity) of available molecular structures. An embodiment may use the properties of available molecular structures to train the RBM (i.e., Gaussian Bernoulli Restricted Boltzman Machine (GBRBM)).

Operation 3: Constructing a DBM by connecting the DBN with the RBM to correlate the molecular structures with the properties. Also, the DBM may be trained with the molecular structures and the properties to predict property values for the given molecular structures.

Figure 7:
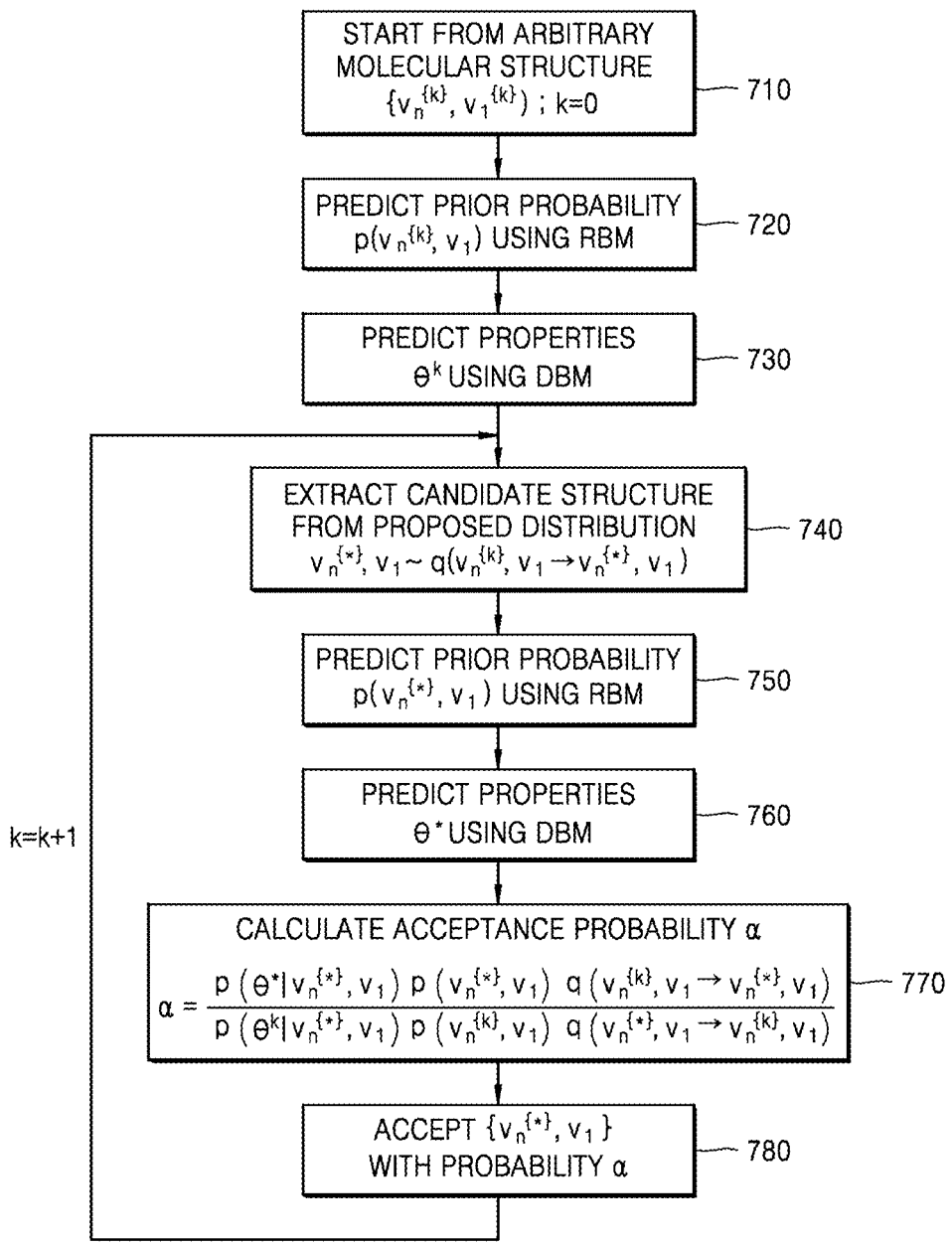
FIG. 7 is a flowchart illustrating a Bayesian inference framework for designing molecules, according to an embodiment.

FIG. 7 is a flowchart illustrating a Bayesian inference framework for designing molecules, according to an embodiment.

An embodiment may use an MCMC technique for sampling from a posterior distribution to generate a sample of molecules with target properties using a Bayesian inference framework.

In operation 710, the MCMC technique may start from an arbitrary molecular structure.

In operation 720, RBM may be used to predict a prior probability of this molecular structure. The prior probability may represent whether the given molecular structures are valid molecular structures. The trained RBM may be used to predict prior probability of the molecular structures.

In operation 730, the properties of the molecular structures may be predicted, and the trained DBM may be used to predict properties of the molecular structures.

In an embodiment, the trained RBM may be used to obtain the prior probability of this molecular structure. In an embodiment, the trained DBM may be used to predict properties of this molecular structure.

Likelihood probability of the predicted property value may be calculated by comparing the predicted property values with the user-specified property values. The posterior probability may be calculated by multiplying the likelihood probability by the prior probability.

In operation 740, a molecule predicted to have the target properties in a proposal distribution may be sampled. More specifically, a proposal molecular structure may be generated by sampling from a heated RBM. Here, the heated RBM may be defined by multiplying weights and biases of the trained RBM by a uniform random number.

In operation 750, a prior probability of the proposal molecule may be predicted. The trained RBM may be used to predict the prior probability of the proposal molecule.

In operation 760, the properties of the proposal molecule may be predicted. The trained DBM may be used to predict the properties of the proposal molecule. The predicted properties of the proposal molecule may be compared with the target properties to obtain the likelihood probability of the proposal molecule. The posterior probability of the proposal molecule may be obtained by multiplying the likelihood probability by the prior probability.

In operation 770, an acceptance probability of the proposal molecule may be calculated. The acceptance probability may be defined as a ratio of the posterior probability of the present molecule to that of the proposal molecule.

In operation 780, the proposal molecule may be accepted as a present state with the probability given by the acceptance probability. This procedure may be repeated by a pre-determined number of iterations.

Figure 8:
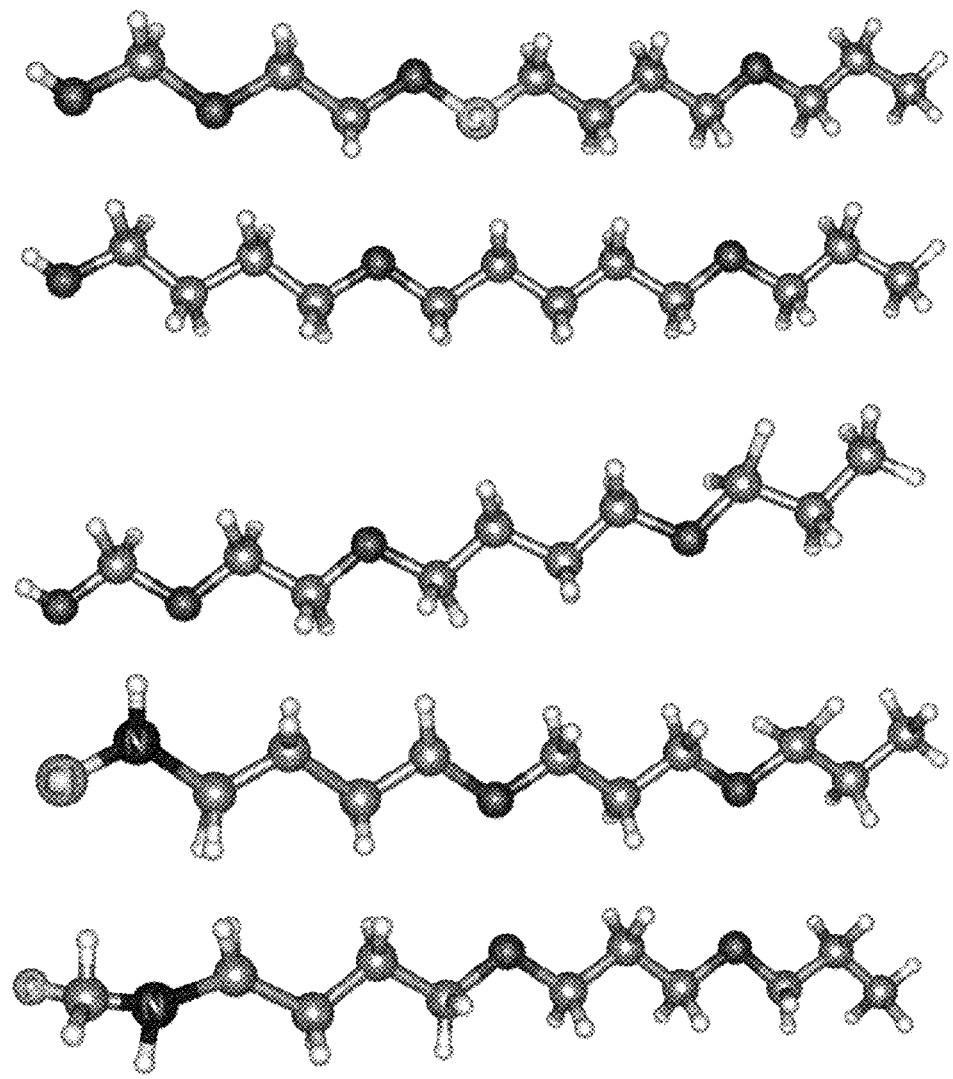
FIG. 8 is a view for illustrating examples of predicted molecules with a redox potential exceeding 4.8 V, according to an embodiment.

FIG. 8 is a view for illustrating examples of predicted molecules with a redox potential exceeding 4.8 V, according to an embodiment.

The system 100 may generate molecules with a redox potential that is greater than or equal to 4.8 V using the Bayesian inference framework.

For example, the Bayesian inference framework may predict totally 5 valid molecular structures with a redox potential that is higher than or equal to 4.8V.

The processes for designing molecules using the machine learning algorithms as described above may be summarized in Table 1, as below.

TABLE 1

| Function | Method |
| --- | --- |
| Molecular Descriptor | Molecular Structure Representation Based on SMILES |
| Structure-Property Correlation | Deep Boltzmann Machine (DBM) |
| Verification on Validity of Molecular Structures | Restricted Boltzmann Machine (RBM) |
| Generate Molecules with Target Properties | Bayesian Inference Using Markov Chain Monte Carlo (MCMC) Method |

As shown in Table 1, a molecular structure may be represented using SMILES as a molecular descriptor.

Information about the correlation between molecular structures and properties of molecules may be acquired by training DBM.

Also, RBM may be used to verify whether the molecular structures are valid molecular structures.

Finally, Bayesian inference using the MCMC method may be used to generate molecules with target properties.

The embodiments may be implemented through at least one software program that is executed on at least one hardware device, and may perform network management functions to control components. Meanwhile, the components shown in FIG. 1 may be at least one of a hardware device or a combination of a hardware device and a software module.

The apparatus according to the present embodiments may include a processor, a memory for storing and executing program data, a permanent storage such as a disc drive, a communication port for communicating with an external device, a user interface (e.g., a key, a button, or the like), etc. The methods implemented by a software module or an algorithm may be stored, as computer-readable codes or program instructions executable on the processor, on a computer-readable recording medium. The computer-readable recording medium may be a magnetic storage medium (e.g., read-only memory ("ROM"), random-access memory ("RAM"), a floppy disc, a hard disc, etc.), an optical reading medium (e.g., CD-ROM and a digital versatile disc ("DVD")), etc. The computer-readable recording medium may be distributed to computer systems connected through a network, and the computer-readable codes may be stored and executed in a distributed manner. The computer-readable recording medium may be readable by the computer, stored in the memory, and executed by the processor.

The present embodiments may be represented by functional block configurations and various processing operations. These functional blocks may be implemented by various numbers of hardware or/and software configurations that execute specific functions. For example, the embodiments may adopt circuit configurations, such as a memory, processing, a logic, a look-up table, etc., which can execute various functions by the control of one or more microprocessors or different control apparatuses. Similarly, that components are executed by software programming or software elements, the current embodiments may be implemented with a programming or scripting language, such as C, C++, Java, assembler, etc., including various algorithms that are realized through combinations of data structures, processes, routines, or other programming structures. Functional aspects may be implemented with an algorithm that is executed by one or more processors. Also, the current embodiments may adopt typical technologies for electronic environment settings, signal processing, and/or data processing, etc. The terms "mechanism", "factor", "means", and "configuration" may be widely used, and may not be limited to mechanical and physical configurations. The terms may include the meaning of a series of routines of software interworking with a processor, etc.

Specific executions described in the present embodiments are examples, and do not limit the technical scope of the present disclosure even in any method. For conciseness of the specification, disclosure of typical electronic configurations, control systems, software, and other functional aspects of the systems may be omitted. In addition, the connection of lines or connection members between the components shown in the drawings illustrate functional connection and/or physical or circuital connections. The connections may be replaced or may be indicated as additional various functional connections, physical connections, or circuit connections in a real apparatus.

In the current specification (particularly, in the claims), the term "said" and the similar directive terms may be used for both the singular and plural forms. Also, the term "range" may include individual values belonging to the "range" (unless the context clearly dictates otherwise). That is, writing a range in the detailed description may be the same as writing individual values constituting the range in the detailed description. Finally, operations constituting the method may be performed in an appropriate order, unless the order of the operations is specified or the context clearly dictates otherwise. That is, the operations may be not necessarily performed in the order in which they are written.

So far, the exemplary embodiments of the present disclosure have been described. However, it will be apparent that those skilled in the art can make various modifications thereto without changing the intrinsic features of the present disclosure. Thus, it should be understood that the exemplary embodiments described above are merely for illustrative purposes and not for limitation purposes. The scope of the present disclosure is defined in the claims rather than the detailed description, and all differences within the equivalent range should be interpreted as belonging to the scope of the present disclosure.

What is claimed is:

1. A method of designing molecules using a machine learning algorithm, the method comprising:
   representing, by a Simplified Molecular Input Line Entry System (SMILES) representation unit, molecular structures included in a dataset by using a SMILES, wherein the SMILES uses a set of characters;
   converting, by a binary representation unit, a SMILES representation of the molecular structures into a binary representation;
   pre-training, by a molecular structure generating unit, a stack of Restricted Boltzmann Machines (RBMs) using the binary representation of the molecular structures to determine a probability density function that estimates whether a candidate molecule comprises a valid molecular structure, the stack of RBMs comprising a three-layer deep belief network (DBN);
   constructing, by the molecular structure generating unit, a four-layer Deep Boltzmann Machine (DBM) by combining the three-layer DBN with a two-layer Gaussian Bernoulli Restricted Boltzmann Machine (GBRBM);
   determining, by the molecular structure generating unit, limited molecular property data by running a Density Functional Theory (DFT) on a subset of the molecule structures in the dataset;
   training, by the molecular structure generating unit, the DBM with the limited molecular property data;
   combining, by the molecular structure generating unit, the pre-trained stack of the RBMs and the trained DBM in a Bayesian inference framework;
   generating, by the molecular structure generating unit, a sample of molecules with target properties by using the Bayesian inference framework; and
   manufacturing, based on the sample of molecules with target properties, one or more real molecules with the target properties.

2. The method of claim 1, further comprising:
   identifying, by the molecular structure generating unit, one or more required substructures; and
   determining, by the molecular structure generating unit, molecules with the target properties and the required substructures by using conditional Markov Chain Monte Carlo (MCMC) sampling.

3. The method of claim 1, further comprising storing, by the molecular structure generating unit, parameters of the pre-trained RBMs.

4. The method of claim 1, further comprising predicting, by the molecular structure generating unit, properties of a given molecule by using the trained DBM.

5. The method of claim 1, wherein pre-training the stack of the RBMs is performed by using a Contrastive divergence algorithm.

6. The method of claim 1, further comprising validating, by the molecular structure generating unit, the molecular structures by using prior probabilities of the molecular structures, wherein the prior probabilities of the molecular structures are obtained using the pre-trained RBMs.

7. A system for designing molecules using a machine learning algorithm, the system comprising:
   a Simplified Molecular Input Line Entry System (SMILES) representation unit which represents molecular structures included in a dataset using a SMILES, wherein the SMILES uses a set of characters;

a binary representation unit which converts a SMILES representation of the molecular structures into a binary representation;

a molecular structure generating unit which pre-trains a stack of Restricted Boltzmann Machines (RBMs) using the binary representation of the molecular structures to determine a probability density function that estimates whether a candidate molecule comprises a valid molecular structure, the stack of RBMs comprising a three-layer deep belief network (DBN), constructs a four-layer Deep Boltzmann Machine (DBM) by combining the three-layer DBN with a two-layer Gaussian Bernoulli Restricted Boltzmann Machine (GBRBM), determines limited molecular property data by running a Density Functional Theory (DFT) on a subset of the molecule structures in the dataset, trains the DBM with the limited molecular property data, combines the pre-trained stack of the RBMs and the trained DBM in a Bayesian inference framework, and generates a sample of molecules with target properties by using the Bayesian inference framework; and a manufacturing unit configured to manufacture, based on the sample of molecules with target properties, one or more real molecules with the target properties.

8. The system of claim 7, wherein the molecular structure generating unit further:
   identifies one or more required substructures; and
   determines a sample of molecules with the target properties and the required substructures by using conditional Markov Chain Monte Carlo (MCMC) sampling.

9. The system of claim 7, wherein the molecular structure generating unit further stores parameters of the pre-trained RBMs.

10. The system of claim 7, wherein the molecular structure generating unit further predicts properties of a given molecule by using the trained DBM.

11. The system of claim 7, wherein the molecular structure generating unit pre-trains the stack of the RBMs by using a Contrastive divergence algorithm.

12. The system of claim 7, wherein the molecular structure generating unit further validates the molecular structures by using prior probabilities of the molecular structures, wherein the prior probabilities of the molecular structures are obtained using the pre-trained RBMs.

* * * * *